(12) United States Patent
Elwell et al.

(10) Patent No.: US 8,157,770 B2
(45) Date of Patent: Apr. 17, 2012

(54) STABILIZATION OF A CATHETER OR CANNULA

(76) Inventors: David G. Elwell, Ada, MI (US); Kim A. Sena, Ada, MI (US)

( * ) Notice: Subject to any disclaimer, the term of this patent is extended or adjusted under 35 U.S.C. 154(b) by 0 days.

(21) Appl. No.: 12/455,275

(22) Filed: May 29, 2009

(65) Prior Publication Data
US 2009/0306602 A1 Dec. 10, 2009

Related U.S. Application Data

(60) Provisional application No. 61/130,841, filed on Jun. 4, 2008.

(51) Int. Cl.
*A61M 5/32* (2006.01)

(52) U.S. Cl. ... 604/180; 604/174; 604/177; 128/DIG. 6; 128/DIG. 26

(58) Field of Classification Search .......... 604/180, 604/177, 179, 272, 508, 174, 304, 307, 308; 128/846, DIG. 6, DIG. 26

See application file for complete search history.

(56) References Cited

U.S. PATENT DOCUMENTS

| | | | |
|---|---|---|---|
| 3,589,361 A | 6/1971 | Loper et al. | |
| 3,973,565 A | 8/1976 | Steer | |
| 4,129,128 A * | 12/1978 | McFarlane | 604/180 |
| 4,490,141 A * | 12/1984 | Lacko et al. | 604/180 |
| 4,698,057 A | 10/1987 | Joishy | |
| 4,737,143 A * | 4/1988 | Russell | 604/180 |
| 4,863,432 A * | 9/1989 | Kvalo | 604/177 |
| 4,932,943 A * | 6/1990 | Nowak | 604/180 |
| 5,087,248 A | 2/1992 | Biesang, III | |
| 5,219,336 A * | 6/1993 | Wilk | 604/180 |
| 5,785,690 A * | 7/1998 | Newman et al. | 604/180 |
| 6,165,156 A | 12/2000 | Cesarczyk et al. | |
| 6,231,548 B1 * | 5/2001 | Bassett | 604/174 |
| 6,582,403 B1 | 6/2003 | Bierman et al. | |
| 6,827,706 B2 | 12/2004 | Tollini | |
| 6,955,659 B1 | 10/2005 | Carter | |
| 7,083,598 B2 | 8/2006 | Liska | |
| 7,153,291 B2 | 12/2006 | Bierman | |
| 7,247,150 B2 | 7/2007 | Bierman | |
| D569,506 S | 5/2008 | Dikeman et al. | |
| 2002/0143295 A1 | 10/2002 | Taylor et al. | |

* cited by examiner

*Primary Examiner* — Kevin C Sirmons
*Assistant Examiner* — Shefali Patel (57) ABSTRACT

A stabilizing device (and method of use) for insertion and maintenance of a catheter or cannula maintains a sterile insertion site and is simple and easy to construct and use, yet optimally maintains the catheter or cannula in place. A first stabilizing element includes a pair of bilateral wings and a catheter or cannula receiving element generally between the wings. A proximal stabilizing element—desirably two distinct and spaced pieces of tape—is operatively connected to the wings and has a sterile adhesive for affixing the wings to a patient to provide stability during needle removal and substantially for the duration that the catheter or cannula is inserted into a patient. A lateral stabilizing element—desirably two pieces of tape—is distinct and spaced from the proximal stabilizing element, to provide primarily lateral and medial stability to a catheter or cannula in a patient. A release sheet may cover the tape adhesive, or the tape may have a pattern of adhesive and non-adhesive sections cooperating with each other. Butterfly catheter, or angiocatheter, embodiments are particularly desirable.

19 Claims, 11 Drawing Sheets

STABILIZATION OF A CATHETER OR CANNULA

CROSS REFERENCE TO RELATED APPLICATION

This application is based upon U.S. Provisional Application Ser. No. 61/130,841, filed Jun. 4, 2008.

BACKGROUND AND SUMMARY OF THE INVENTION

Conventional commercial procedures for inserting and maintaining catheters or cannulae in patients are often cumbersome, time consuming, inefficient, and less than optimally hygienic. For example, in a typical conventional procedure for inserting and maintaining an angiocatheter in a human patient to connect the patient to an IV (as generally described in U.S. Pat. Nos. 4,772,264 and 7,491,189), a needle of an insertion device within the angiocatheter is inserted into the patient's vein at a low angle. Once this cannulized needle has been inserted, one advances the angiocatheter approximately two cm to allow the catheter to enter into the vessel lumen. Then one places pressure at the tip of the catheter, and while securing the catheter with one's fingers removes the needle from the vein and catheter, leaving the catheter in place. Then one quickly connects the IV tubing to the catheter and attempts to secure the catheter with tape. This requires obtaining a piece of tape from a separate source (often placed by the practitioner on nearby non-sterile surfaces), trying to properly position the tape using one hand while stabilizing the catheter with the other (or requiring the assistance of another health care practitioner), and then positioning one or more other pieces of tape over the catheter at other, possibly random, locations. Not only is this procedure cumbersome and inefficient, there is a distinct possibility of contamination of the insertion site during the taping procedure.

A number of prior art proposals have sought to minimize the disadvantages of conventional procedures, such as the one described above, using more sophisticated devices. For example, such as shown in U.S. Pat. No. 6,231,548 an anchor pad having wings may be utilized to facilitate the taping procedure. U.S. Pat. No. 3,973,565 proposes using a butterfly catheter with a trailing scored sheet having pressure sensitive adhesive whereby after insertion a release sheet can be removed from the adhesive and the trailing sheet folded over about the score lines to bring the adhesive into contact with the patient's skin adjacent the insertion site (in fact typically covering it); compare FIGS. 3 & 4 thereof. U.S. Pat. No. 6,827,706 in FIGS. 19-21, and U.S. Pat. No. 3,589,361 in FIGS. 8-11 thereof, show a butterfly catheter having adhesive covered by a release sheet on what will become the inferior surface of the wings to provide primarily lateral stability to the catheter when inserted. U.S. Pat. Nos. 7,083,598, 6,582, 403, 6,955,659, and 4,698,057, and U.S. Patent Application Publication 2002/0143295, show other devices using some form of adhesive element operatively connected to a catheter or cannula to facilitate stabilization. However all of these either have adhesive elements that are almost as difficult to use (or perhaps even more difficult) as conventional pieces of tape, obscure the insertion area and/or the stabilization junctures, could interfere with optimal catheter insertion or repositioning, require catheter elements per se to have adhesive, lack versatility, and/or don't afford optimal stabilization in all the dimensions necessary.

According to the present invention, a stabilizing device for insertion and maintenance of a catheter or cannula, and a method of utilization thereof, are provided which overcome all or most of the drawbacks of the prior art. In general, the invention is simple, relatively inexpensive, versatile, and provides optimal stabilization.

While the invention will be described primarily with respect to angiocatheters and butterfly catheters, it is to be understood that these are representative only, and the invention is applicable to a wide variety of catheters and cannulae.

According to one aspect of the present invention there is provided a stabilizing device for insertion and maintenance of a catheter or cannula, comprising: A first stabilizing element including a pair of bilateral wings and a catheter or cannula receiving element generally between the bilateral wings. A proximal stabilizing element operatively connected to at least one of the bilateral wings and including a sterile adhesive for affixing at least one of the bilateral wings to a patient to provide stability for the catheter or cannula during the removal of the needle and for the duration that the catheter or cannula is inserted into the patient. And, a lateral stabilizing element distinct and spaced from the proximal stabilizing element, the lateral stabilizing element including a sterile adhesive for affixing at least one (and preferably both) of the bilateral wings to a patient to provide primarily lateral and medial stability to a catheter or cannula in a patient. The separation of the proximal and lateral stabilizing elements allows the proximal elements to be applied first. Then, lateral and superior adjustments can be made to the needle and catheter or cannula (i.e. to better establish blood flow therethrough), as well as cleaning of blood or IV fluid below the device hub or base, before the lateral stabilizing elements are secured. By providing spaced and distinct lateral and proximal stabilizing elements, the invention allows clear visibility of the insertion site (to facilitate insertion, withdrawal, cleaning of spillage, and adjustment), yet readily provides essentially optimum stability.

While the proximal and lateral stabilizing elements may comprise integral portions of the bilateral wings (and/or the receiving element), or have other configurations, preferably they are provided by conventional pieces of tape pre-applied to the wings (that is applied during manufacture, or before insertion by the health care practitioner). The tape strips may have non-adhesive portions thereof facilitating removal of the tape strips from a patient's skin when desired.

In a preferred embodiment the proximal stabilizing element comprises at least first and second distinct and spaced tape strips with pressure sensitive sterile adhesive on portions thereof proximally overlapping the bilateral wings, one connected to each of the bilateral wings. The proximal tape strips—as the name indicates—extend toward the insertion site, that is are "proximate" to it. Also in this preferred embodiment, the lateral stabilizing element comprises at least third and fourth distinct and spaced tape strips with pressure sensitive sterile adhesive on portions thereof laterally overlapping the bilateral wings, one connected to each of the wings. Where the tape strips are generally quadrate the overlapping portions of the lateral strips may extend substantially transverse to the first and second tape strips. The lateral tape strips—again as the name indicates—extend laterally of the insertion site. Most desirably the proximal stabilizing element consists essentially of the first and second strips (i.e. there are only two), and the lateral stabilizing element consists essentially of the third and fourth strips (i.e. only two). The first and second proximal strips provide primarily proximal and distal stability, while the third and fourth lateral strips provide primarily medial and lateral stability.

The configuration of the tape strips may vary considerably, for example to increase stability by providing an increases adhesive surface area, to enhance visibility, or to improve other functions. They may be rectangular, partially rectangular and partially trapezoidal, or have a variety of other configurations. Also, especially the proximal tape strips need not necessarily extend parallel to the catheter (although that may be desirable to serve as a guide for needle insertion); for example they may extend at an angle of about 10-45 degrees. Also, fold lines may be provided on the tape strips to allow them to be easily and precisely folded out of the way during the insertion procedure.

The device may further comprise a separate release sheet covering adhesive on each of the tape strips to maintain sterility and enhance functionality. Along one or both side edges of the tape strips continuous or spaced non-adhesive areas may be provided. This makes grasping of a release sheet easier, and also allows ready removal of the tape from the patient's skin after the catheter has been removed.

Alternatively instead of a release sheet at least one (and maybe all) of the tape strips may have a bottom (inferior) surface with a pattern of pressure sensitive adhesive and release sections. The tape strip with this pattern is folded over on itself so that the adhesive and release sections operatively engage each other to maintain sterility until unfolded to be affixed to a patient's pre-sterilized skin.

Again, while a wide variety of constructions may be used, the device of the invention is desirably used in combination with an angiocatheter or a butterfly catheter. [Butterfly catheters derive their name from the highly flexible plastic wings extending laterally outwardly from the sides of a hollow needle (the hollow needle forming at least part of the catheter). Exemplary prior art butterfly catheters are shown in U.S. Pat. Nos. 3,589,361, 3,973,565, 4,177,809, 4,698,057, 6,743,209, and 6,827,706.]

The device of the invention may further comprise at least fifth and sixth distinct and spaced distal tape strips, one operatively connected to each of the bilateral wings and having a portion thereof with pressure sensitive adhesive distally overlapping a wing. As the name indicates, the distal strips are remote from the insertion site and extend away from it (i.e. distally). Also, the device may further comprise at least seventh or eighth transverse tape strips, one each operatively connected to each of the bilateral wings and having a portion thereof with pressure sensitive adhesive overlapping a wing. These strips are remote to the insertion sight and extend diagonally across the cannula hub and attach on the opposite side of the hub.

The receiving element of the device preferably comprises a substantially tubular hub or base, and a catheter extending proximally from the base. When the insertion device is an angiocatheter or the like, typically at some point the device is in combination with a conventional catheter insertion device having a needle extending through the base and catheter. The needle is withdrawn from the combination (and a piece of IV tubing operatively connected to the catheter hub or base) once the patient's skin has been penetrated, and the catheter properly advanced into place.

According to another aspect of the invention there is provided a method of stabilizing a catheter or cannula in a patient (human or animal) using a first stabilizing element having bilateral wings extending from a catheter or cannula supporting element, and at least one each of distinct and spaced proximal and lateral stabilizing elements having sterile pressure sensitive adhesive associated therewith, comprising: a) Inserting a catheter or cannula associated with the supporting element into the patient's body adjacent the at least one proximal stabilizing element. Then, b) applying the sterile adhesive from the at least one proximal stabilizing element to a patient's skin adjacent an area of insertion of a catheter or cannula to stabilize against catheter or cannula inadvertent withdrawal or adverse repositioning. And then c) applying the sterile adhesive from the at least one lateral stabilizing element to the patient's skin to provide primarily lateral and medial stability to the catheter or cannula.

In one embodiment, especially when placing an angiocatheter, b) is practiced using a removable insertion device with a needle, and the method further comprises d) removing the removable insertion device after b) and before c), or after c). The method typically further comprising e) lifting the receiving element and removing any blood flash or IV fluid from the patient's skin between b) and c), and the distinct and spaced proximal and lateral stabilizing elements allow this procedure to be accomplished quickly and easily without disturbing the insertion site, and with optimum probability of maintaining sterility.

In this method, most desirably, the supporting element supports an angiocatheter and the at least one proximal stabilizing element comprises first and second distinct and spaced proximal tape strips each having a portion with sterile pressure sensitive adhesive overlapping a bilateral wing, and the at least one lateral stabilizing element comprises third and fourth distinct and spaced lateral tape strips each having a portion with sterile pressure sensitive adhesive overlapping a bilateral wing. In this case, in the method, b) is practiced to separately bring the sterile adhesive of each of the first and second tape strips into contact with a patient's skin; c) is practiced to separately bring the sterile adhesive of each of the third and fourth tape strips into contact with a patient's skin; and a)-c) are practiced to insert into, and maintain within a patient, an angiocatheter.

According to a further aspect of the invention there is provided a stabilizing device for insertion and maintenance of a catheter or cannula, comprising: A stabilizing element including a pair of bilateral wings and a catheter or cannula supporting element generally between the bilateral wings. And at least first and second spaced and distinct tape strips, operatively connected to at least one bilateral wing preferably both for bilateral support) for stabilizing the receiving element, the tape strips each having a bottom surface with a pattern of pressure sensitive adhesive and release sections, and being folded over on itself so that the adhesive and release sections operatively engage each other to maintain sterility, and after unfolding affix the tape strips to a patient's skin with the pressure sensitive adhesive sections. This pattern of adhesive and non-adhesive portions eliminates the need for a release sheet while still providing sterility and ready utilization of the device. As described above, preferably the at least first and second tape strips comprise a pair of spaced and distinct proximal tape strips, and a pair of spaced and distinct lateral tape strips.

According to yet another aspect of the invention, there is provided a butterfly catheter having a base and highly flexible wings with superior and inferior surfaces. This butterfly catheter comprises: At least two spaced, distinct, pieces of adhesive tape, with sterile adhesive. And at least one piece of adhesive tape operatively connected to the superior surface of each of the flexible wings and each including a portion with sterile pressure sensitive adhesive overlapping a flexible wing so that the sterile adhesive on the overlapping portion may be affixed to a patient's skin. In a preferred form of the butterfly catheter according to the invention the at least two spaced, distinct, pieces of adhesive tape comprise only two proximal pieces (one on the left and one on the right of the hub), proximal pieces being most desirably for providing stability of a butterfly catheter in the case of distal and even proximal movement of the apparatus. However this device may also include two lateral pieces for stabilizing against medial and lateral movement, and perhaps even two distal pieces. As with other embodiments, the overlapping adhesive of the tape strips is covered with a release sheet, or the tape strips are folded over and have the pattern of adhesive and non-adhesive sections described above.

The following specific advantages (over one or more prior art devices or procedures) may be expected according to the invention:

Maintains a sterile field. The practitioner's sterile-gloved hands use only sterile, pre-applied tape according to the invention, insuring that the practitioner's sterile hands do not leave the sterile field, minimizing entry of MRSA or other infectious agents.

Minimizes the use of tape in general, and in particular minimizes the use of sterile tape, and minimizes the time for applying the tape while maximizing the chances of success of the associated medical procedure;

Provides for substantially immediate and effective stabilization of the catheter after insertion (and after withdrawal of the needle when inserting an angiocatheter). In particular the proximal tape strips are positioned so that they are readily accessible, and provide optimal bilateral stability against inadvertent displacement of the catheter, while still continuously allowing a clear view of the insertion area. Because the tape strips are attached to the first stabilizing element wings, and not directly to the receiving element, the receiving element is easy for the practitioner to grasp with her/his fingers during insertion, and also to hold the catheter in place during proximal and lateral tape attachment.

As a result of the advantages of the invention, the field is completely sterile and the catheter completely stable, so that an occlusive sterile dressing (e.g. a sterile transparent bandage) can ultimately be placed over the field with no pathogens near the insertion area.

It is the primary object of the present invention to provide a simple, versatile, and effective stabilizing device for a catheter or cannula, and/or a catheter or cannula in combination therewith, as well as a method of utilization thereof. This and other objects of the invention will become clear from an inspection of the detailed description of the drawings, and from the appended claims.

DETAILED DESCRIPTION OF THE DRAWINGS

Figure 1:
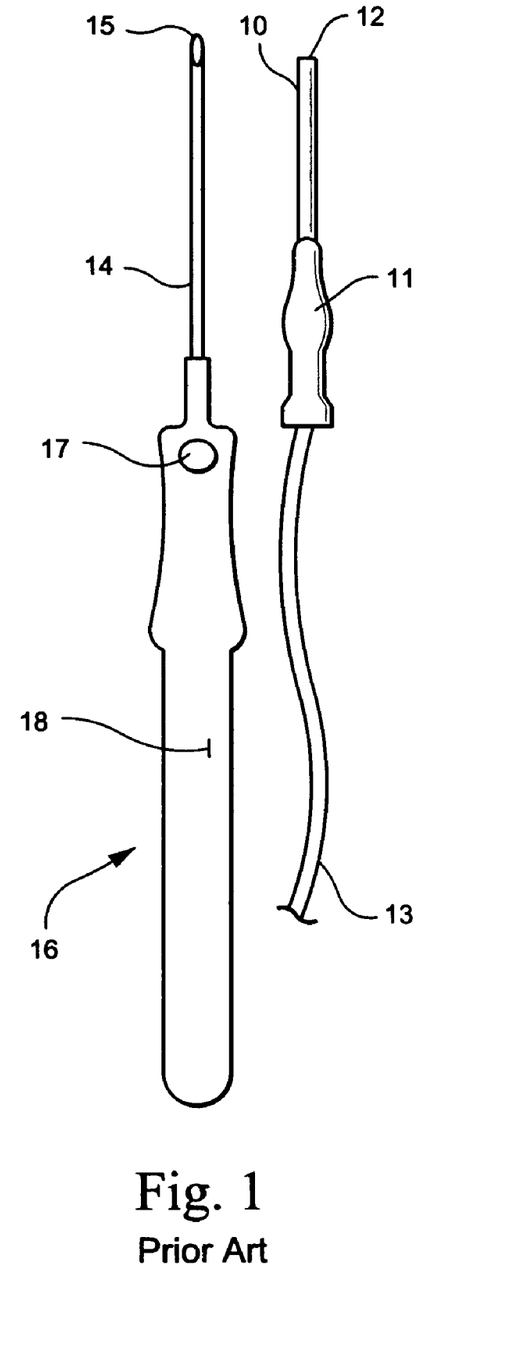
FIG. 1 is a top plan (superior) view of an exemplary prior art angiocatheter and an insertion device utilizable therewith.

FIG. 1 shows a conventional angiocatheter assembly comprising a catheter element (10-13) and an insertion element (14-18). One exemplary commercial conventional assembly is that manufactured by Becton Dickinson, referred to as the BD Insyte Autoguard (e.g. 18 gauge). A catheter 10 is received by a base or hub 11 and has a free end 12 which will—during use—extend into a patient's blood vessel or body cavity. Since both the base 11 and catheter 10 are tubular, after insertion a piece of IV tubing (which may be called an IV catheter) 13 connects to the hollow interior of the base 11 and provides flow of fluid to (e.g. from an IV bag) or from the catheter 10.

During insertion, the needle 14 of the insertion device 16 extends through the hollow interiors of the catheter 10 and base 11 so that the sharp tip 15 of the needle 14 extends past the end of the catheter 10. A button 17 is located on the handle 18 of the insertion device 14 which when pushed releases a loaded spring (not shown) to effect quick retraction of the needle 14 so that the tip 15 thereof retracts to the interior of the catheter 10 (that is the tip 15, no longer extends past the free end 12 of the catheter 10).

Typically the needle 14, and some other components, of the insertion device 16 are made of steel, while the base 11, catheter 10, and tubing 13, are of medical grade plastic. The base 11 may have serrations or other surface manifestations to facilitate gripping thereof (as may the handle 18 of the insertion device 16).

Figure 2:
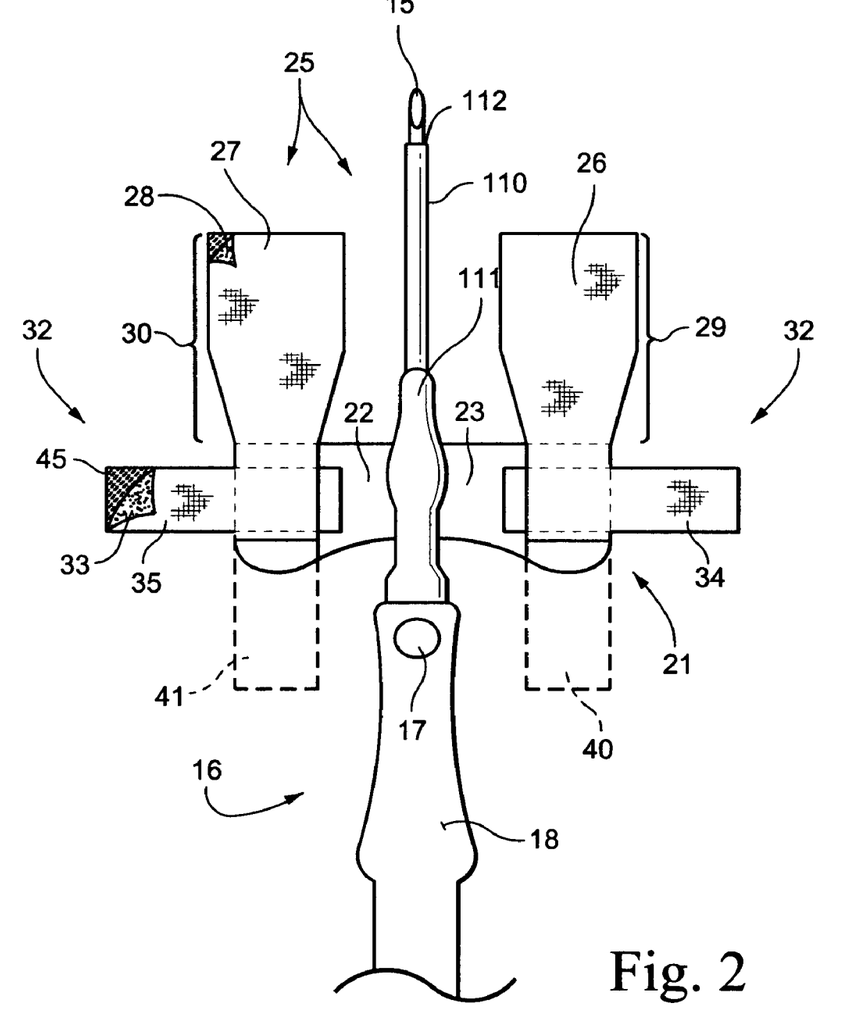
FIG. 2 is top plan view of an assembly comprising the prior art insertion device of FIG. 1 in combination with an exemplary catheter stabilizing device according to the invention with proximate and lateral stabilizing elements shown in solid line, and a distal stabilizing element in dotted line.

FIG. 2 shows the insertion device 16 in combination with a stabilizing device for insertion and maintenance of a catheter or cannula, the stabilizing device shown generally by the reference numeral 21. In this embodiment the device 21 includes a catheter 110 with a free end 112 and a base 111, which element 111 may also be called a catheter receiving element. [Components of the device 21 in FIG. 2 comparable to those in FIG. 1 are shown by the same reference numeral preceded by a "1"].

A first stabilizing element of the device 21 comprises the catheter receiving element 111 and the bilateral wings 22, 23, operatively connected to the element 111. While as shown the wings 22, 23 typically are integral with the element 111, and made of approximately or essentially the same material (e.g. a medical grade plastic), other configurations are possible. For example, the wings 22, 23 may be attached to the element 111 by any suitable conventional mechanisms, such as snaps, hook and loop fasteners (e.g. VELCRO® fasteners), and bayonet coupling connectors. The wings 22, 23 may have a wide variety of shapes and dimensions, which may vary depending upon the catheter or cannula, or procedure, used. While in the FIGS. 2-7 embodiment the wings 22, 23 are preferably of a somewhat flexible plastic (although not as flexible as the plastic of a butterfly catheter), they may be of a substantially rigid material.

The device 21 also includes a proximal stabilizing element (shown generally by reference numeral 25) operatively connected to at least one of the bilateral wings 22, 23 and including a sterile conventional adhesive (preferably pressure sensitive) for affixing at least one of the bilateral wings 22, 23 to a patient (human or animal) to provide primarily proximal and distal stability for insertion of a catheter or cannula into the patient.

While the proximal stabilizing element 25 could be an integral projection from one or both of the wings 22, 23 with adhesive on the inferior surface thereof—or have another configuration which accomplishes the desired purpose—in the preferred embodiment illustrated in the drawings the element 25 comprises at least first and second distinct and spaced conventional medical grade tape strips 26, 27, respectively, with pressure sensitive sterile adhesive (see at 28 in FIGS. 2 & 3), one connected to each of the bilateral wings 22, 23. The adhesive 28 is provided on at least portions 29, 30 of the tape strips 26, 27, respectively, proximally overlapping the wings 22, 23. In the most preferred embodiment only two tape strips 26, 27 are provided. As illustrated in FIGS. 2-7, and as the name indicates, the proximal strips 26, 27 extend from the wings 22, 23 toward the insertion site (and the free end 112 of the catheter 110) and are most proximate the insertion site.

The fact that there are distinct and spaced tape strips 26, 27 provides a number of advantages. For example, the insertion site always remains visible, even after insertion, and the adhesive (28) on the strips 26, 27 may be applied more precisely than if a large adhesive-backed sheet were utilized. Also, the proximal direction of elongation of the strips 26, 27 allows for substantially immediate yet secure affixation of the catheter 110 in place once inserted. Still further, conventional medical grade tape may be utilized and may be applied during manufacture of the element 111 and wings 22, 23, or may be pre-applied shortly before the insertion procedure.

Figure 3:
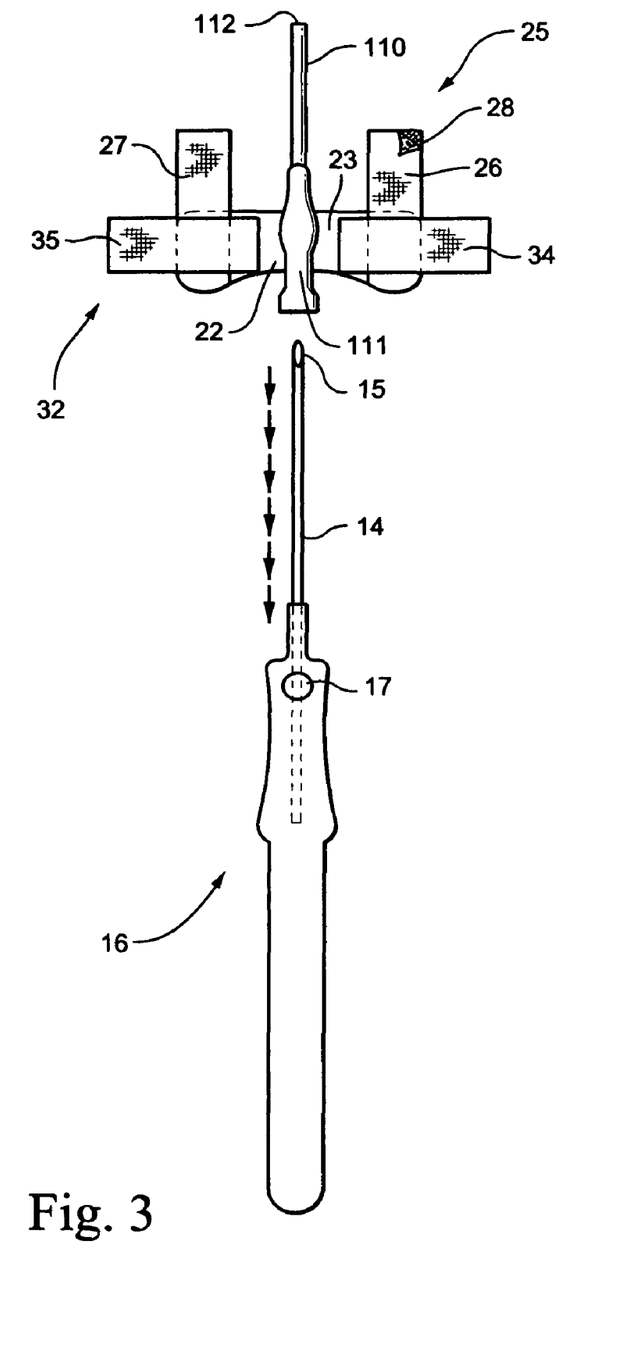
FIG. 3 is an exploded view of the inventive stabilizing device and prior art insertion device of FIG. 2 (without the distal stabilizing element)

The device 21 also includes a lateral stabilizing element—shown schematically at 32 in FIGS. 2 & 3—distinct and spaced from the proximal stabilizing element 25. The lateral stabilizing element 32 includes a sterile adhesive 33 (see FIG. 2) for affixing at least one of the bilateral wings 22, 23 to a patient to provide primarily medial and lateral stability to a catheter (e.g. 110) or cannula in a patient. In the preferred embodiment illustrated in FIGS. 2 & 3, the element 32 preferably comprises at least third and fourth distinct and spaced tape strips 34, 35 with pressure sensitive sterile adhesive (33) on portions thereof laterally overlapping the bilateral wings 22, 23, one connected to each of the wings 22, 23. In the most preferred embodiment only two tape strips 34, 35 are provided. As illustrated in FIGS. 2-7, and as the name indicates, the lateral strips 34, 35 extend generally laterally from the wings 22, 23 and generally to the sides of (and remote from) the insertion site (and the free end 112 of the catheter 110).

The device 21 may also optionally comprise at least fifth and sixth distinct and spaced distal tape strips 40, 41, shown in dotted line in FIG. 2, one operatively connected to each of the bilateral wings 22, 23. Each strip 40, 41 has a portion 42, 43, respectively, thereof with pressure sensitive adhesive distally overlapping a wing 22, 23. As the name indicates, the distal strips 40, 41 extend generally away from the insertion site and catheter 110 free end 112.

Figure 4:
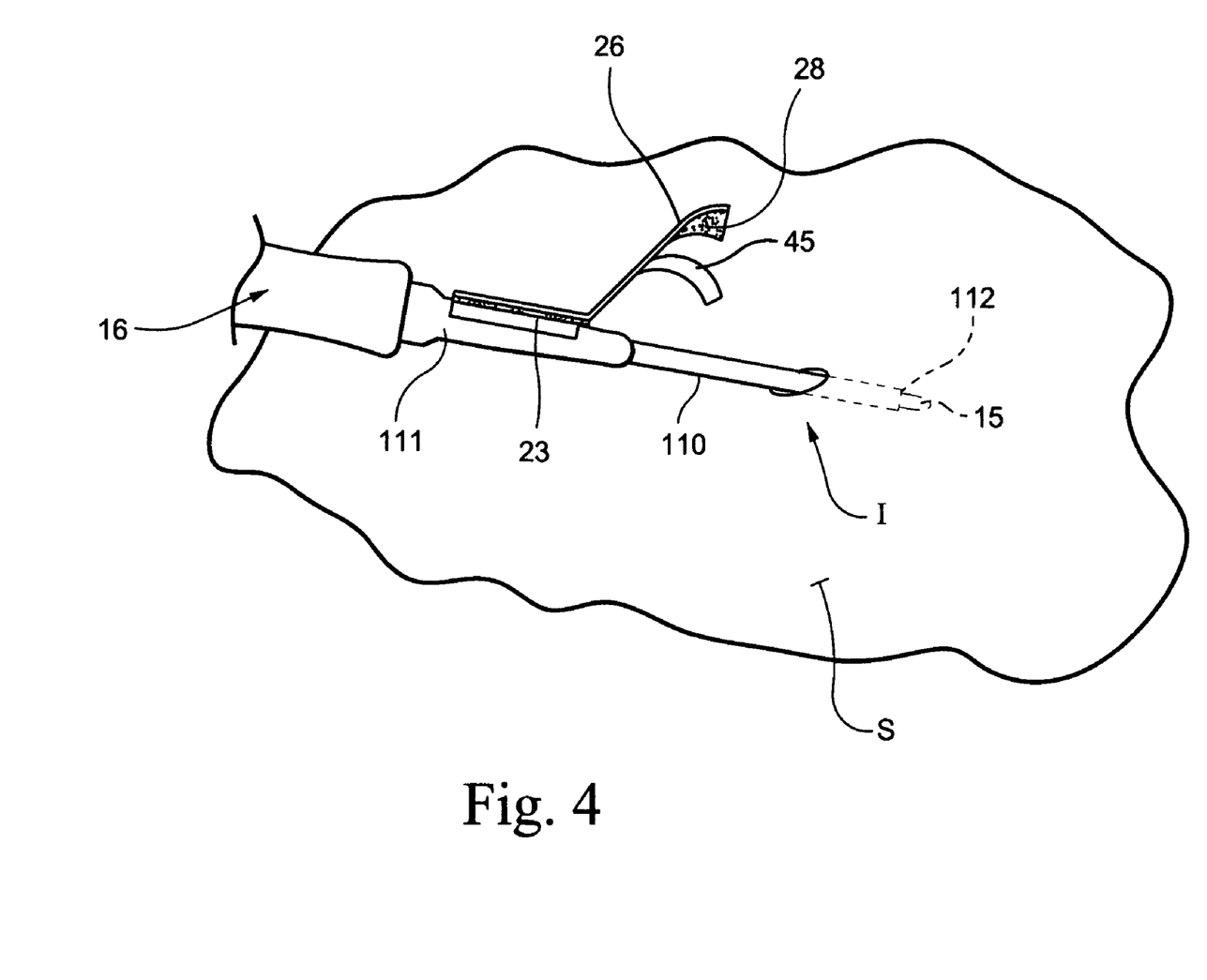
FIG. 4 is a partial side view of the assembly of FIG. 3 during insertion of the needle of the insertion device into a patient's skin (shown isometrically) to position an angiocatheter, and showing the nearest proximal piece of tape slightly twisted to reveal its adhesive as the release sheet is being removed (and not illustrating the lateral tape or some other elements for simplicity of illustration)
Figure 5:
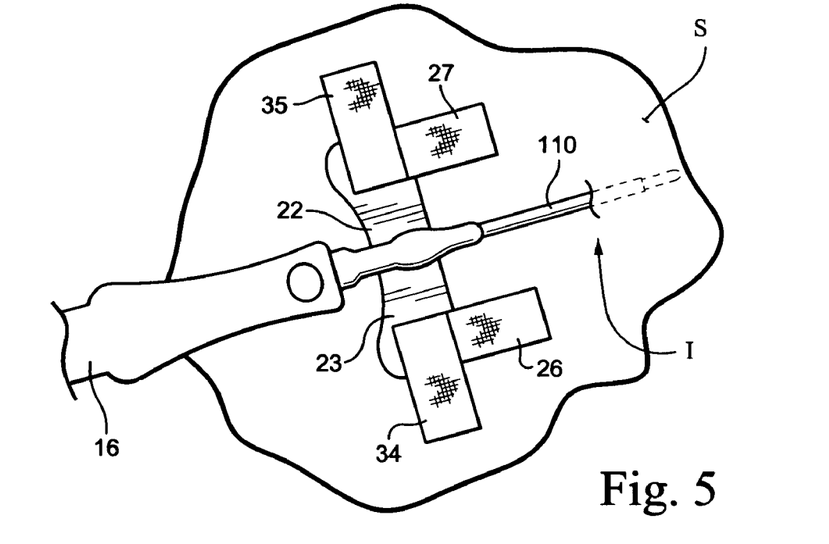
FIG. 5 is a top plan view like that of FIG. 4 showing the proximal and lateral pieces of tape prior to affixation thereof to a patient's skin.

All of the adhesive portions (e.g. 28, 33) of the various tape strips (26, 27, 34, 35, 40 & 41) are typically covered with a conventional release sheet—one shown schematically at 45 in FIGS. 2 & 4. However other manners of maintaining the adhesive sterile and inactive until ready for use may also be provided, some of which will be hereinafter described.

FIGS. 4-7 schematically illustrate an exemplary manner of using the device 21 in a medical procedure (in this example to operatively connect an IV to a patient). Using the combination of FIG. 2, with the bevel of the needle tip 15 facing away from the skin S of the patient, one grasps the handle 18 and moves it toward the skin S, inserting the needle tip 15 into the patient's vein (V in FIG. 7) or other vessel at a low angle (approximately fifteen degrees—see FIG. 4) at an insertion site I. Once the vein V is entered blood will flow into the angiocatheter 110 (called flashback). At this point only the needle 14 of the angiocatheter combination of FIG. 2 is within the vein, therefore the combination is advanced by moving the handle 18 approximately two cm to allow the catheter 110 free end 112 to enter into the vessel lumen. This is the position illustrated in FIGS. 4 & 5.

The practitioner then holds the base 111 with the fingers on one hand and then one at a time removes the release sheets 45 from the proximal tape strips 26, 27 with the fingers of the other hand (FIG. 4 shows the release sheet of the strip 26 being removed to expose the adhesive 28 on the bottom of the strip 26), pushing the adhesive 28 into affixing contact with the skin S. The proximate strips 26, 27 aid in restricting undesirable movement of the cannula 110, and stability during withdrawal of needle 14.

Figure 6:
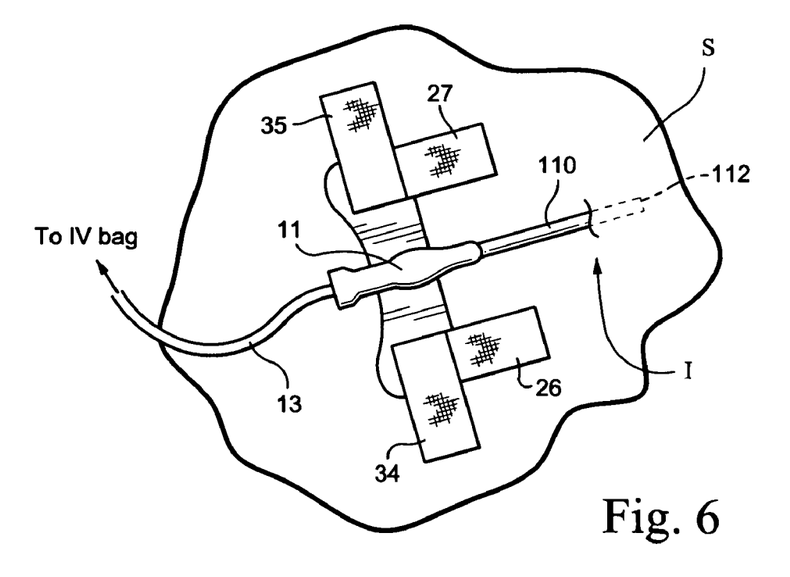
FIG. 6 is a view like that of FIG. 5 only after the insertion device has been removed and a piece of surgical tubing operatively connected to the catheter, and with the proximal and lateral pieces of tape affixed to the patient's skin.

In a preferred method, once the proximate strips 26, 27 are affixed to the skin S the practitioner pushes the button 17, causing the needle 14 to be retracted fully into the catheter 110. Then the entire device 16 is removed and the IV tubing 13 connected to the element 112 (as is conventional per se), as seen in FIG. 6. Regardless of exactly when the insertion device 16 is removed, the practitioner lifts the receiving element 111 and removes any blood flash or IV fluid from the patient's skin S prior to affixing the lateral strips 34, 35 to the skin S.

Figure 7:
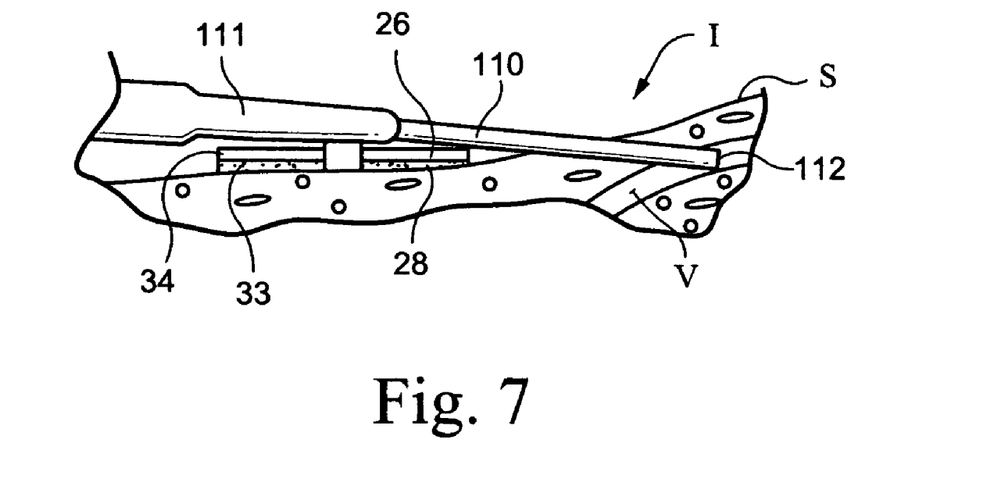
FIG. 7 is a side view comparable to the plan view of FIG. 6, with a portion of the patient shown in cross-section, and showing the catheter inserted within a blood vessel and schematically showing the adhesive of the closest proximal and lateral strips of tape affixed to the patient's skin, with other elements not illustrated in order to more clearly show these features.

After any blood flash or IV fluid is removed, the release sheets 45 are removed one at a time from the lateral tape strips 34, 35, and the adhesive 33 on the bottoms thereof pressed onto the skin S to further stabilize the catheter 110. If desired, the insertion device 16 may be removed after the lateral strips 34, 35 are affixed to the skin S—see FIG. 6—instead of before. If distal strips 40, 41 are provided, the release sheets are removed therefrom and they are affixed to the skin S too. The final configuration is as illustrated in FIG. 7, and then—as is conventional—a sterile transparent bandage (not shown) can be placed over the entire area illustrated in FIG. 7 with no pathogens near the insertion site I.

FIGS. 8-13 show further modifications and details for stabilization of an angiocatheter or the like according to the invention.

Figure 8:
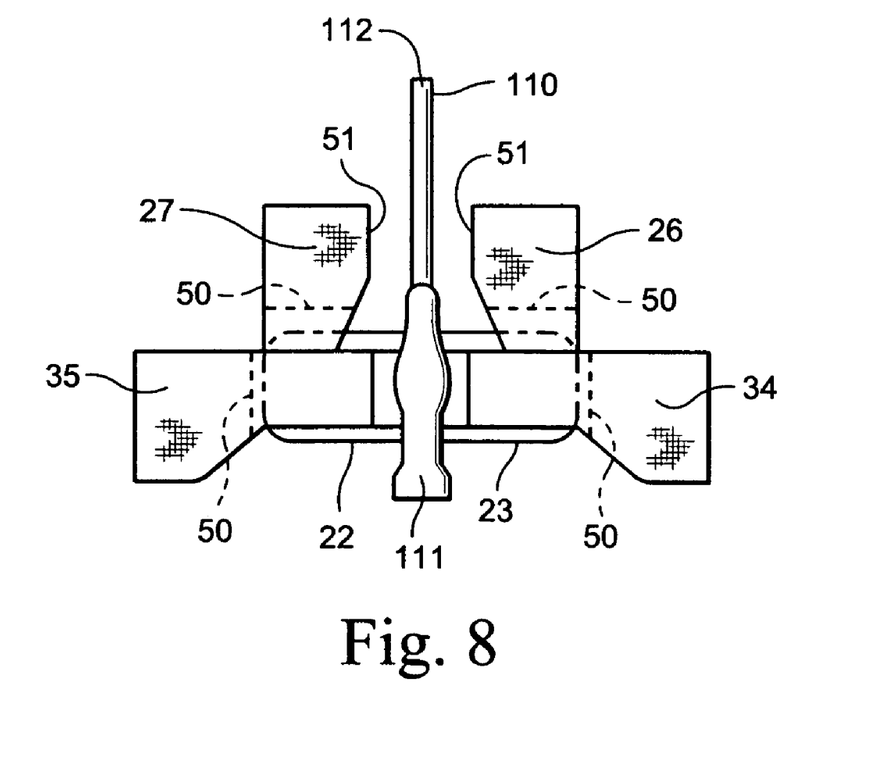
FIG. 8 is a top plan view of a device like that of FIGS. 2 & 3 but having a slightly modified form.

In the FIG. 8 embodiment instead of the tape strips 26, 27, 34, 35 being substantially rectangular, or rectangular and then trapezoidal at the overlapping portions thereof, as in earlier figures, the strips 26, 27, 34, 35 are rectangular, trapezoidal, and then rectangular again, and provide a larger area for affixation to skin S. A crease, score line, fold line, or the like, 50 is provided for each strip 26, 27, 34, 35 to facilitate superior folding of the overlapping portions thereof (as seen in FIG. 4) to in turn facilitate use. Also, the medial edges 51 are substantially parallel to the catheter 110 to serve as a guide for insertion of the needle 14 into a vein V (while still allowing a clear view of the insertion site I).

A wide variety of other configurations of the tape strips are also possible.

Figure 9:
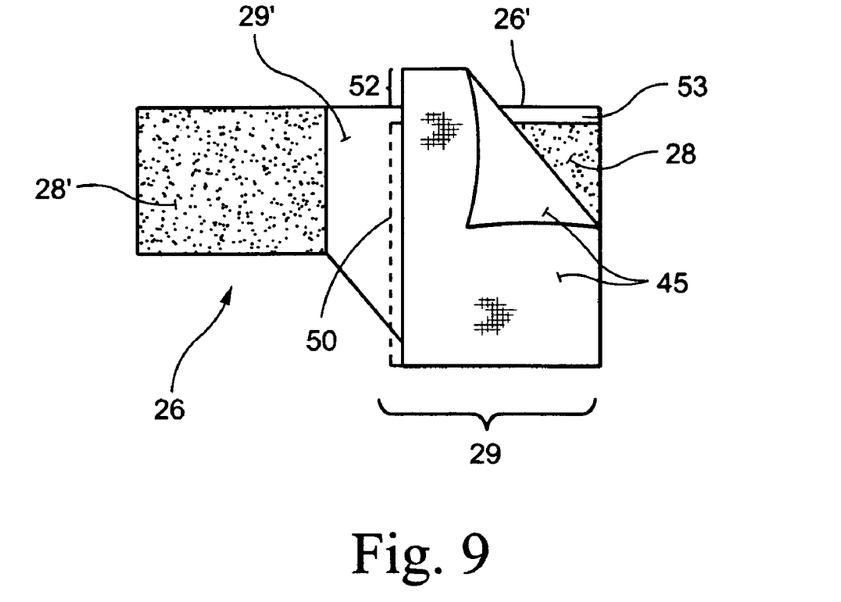
FIG. 9 is a bottom plan view of an isolated modified exemplary piece of tape utilized according to the invention with a release sheet shown being peeled away.

FIG. 9 shows in detail a slight modification of the tape strip 26 of FIG. 8 to enhance utilization even further. The release sheet 45 covering the adhesive 28 on the overlapping portion 29 of the strip 26 is wider than the strip 26 so that a portion 52 thereof extends past an edge 26' of the strip 26 for easy grasping of the sheet 45 for removal. Also, at the edge 26' is a non-adhesive portion 53 of the strip 26 inferior surface. The portion 53 not only facilitates removal of the strip 26 from a patient's skin S after total completion of a medical procedure, but also makes removal of the release sheet 45 simpler. FIG. 9 also shows an optional non-adhesive space 29' between the adhesive 28' which connects the strip 26 to the wing 23, and the line 50 and adhesive 28 (which will affix the tape 26 to the skin S).

Figure 12:
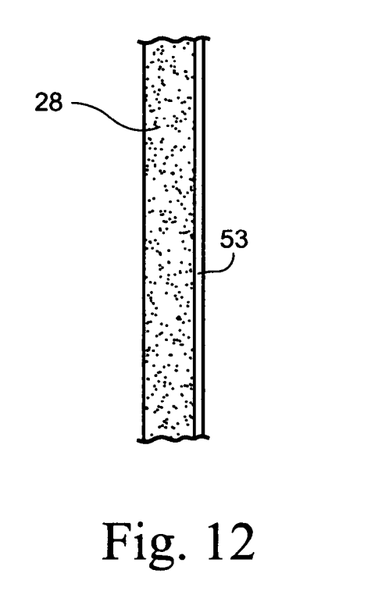
FIG. 12 is a bottom (inferior) view of showing a tape strip which may be used according to the invention with a substantially continuous non-adhesive area along an edge thereof to facilitate removal of a release sheet and/or removal of the tape from a patient's skin after catheter withdrawal.
Figure 13:
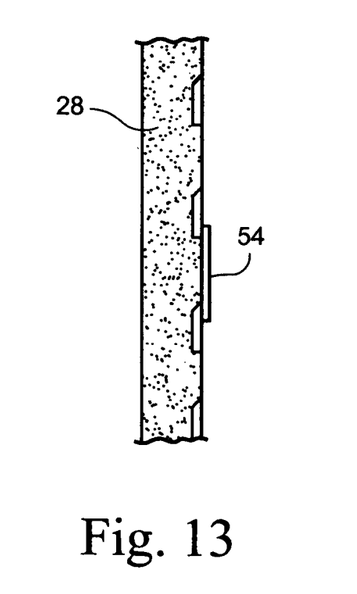
FIG. 13 is a view like that of FIG. 12 only with spaced non-adhesive portions along an edge thereof.

The configuration of FIG. 9 can be used for all the tape strips according to the invention. FIG. 12 shows a rectangular tape strip having adhesive 28, with a non-adhesive portion 53 continuous along one longitudinal edge thereof, while FIG. 13 shows a modification having non-adhesive portions 54 along one edge spaced from each other.

Figure 10:
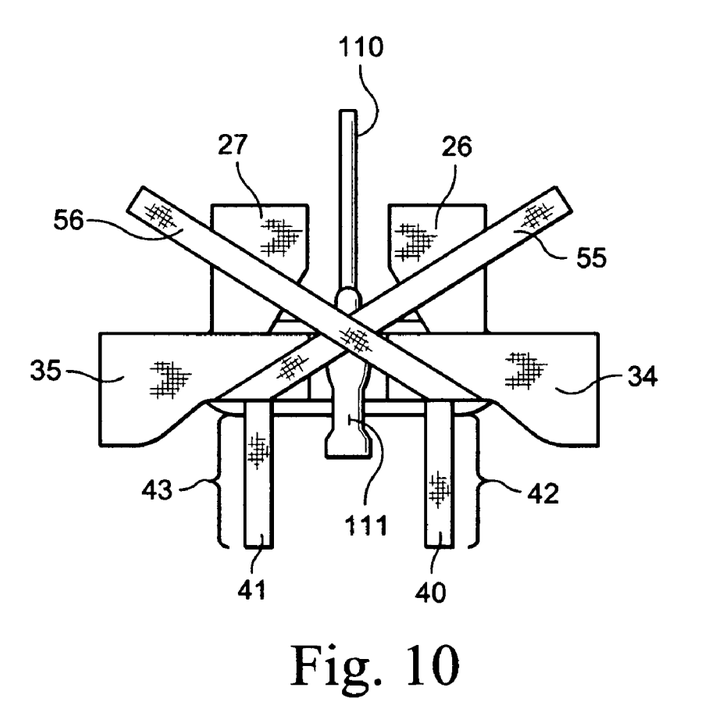
FIGS. 10 & 11 are views like that of FIG. 8 of other modification of the inventions.

FIG. 10 shows another modification of the invention like that of FIG. 8 wherein in addition to distal tape strips 40, 41 there are angled proximate tape strips 55, 56.

Figure 11:
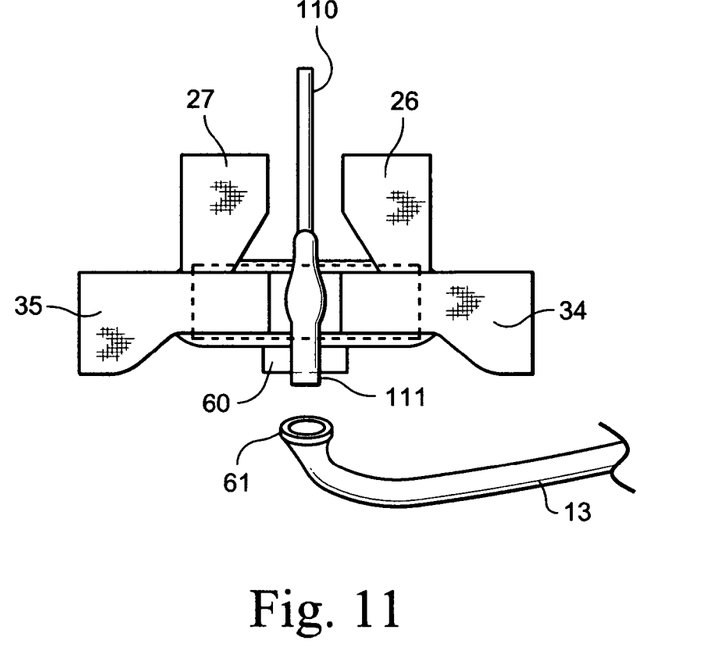

FIG. 11 shows another modification of the invention like that of FIG. 8 wherein a foam pad 60 is provided which extends from the inferior surface of the wings 22, 23. The foam pad 60 minimizes abrasion between the skin S and the element 111 when the catheter 110 is in place in the patient for a long period of time. In the FIG. 11 embodiment the tubing 13 has a female end 61 which fits over the distal end of the element 111. If instead the distal end of the element 111 is the female portion of a connector and the end of the tubing 13 the male portion, then the pad 60 extends past the distal end of the element 111 to perform its abrasion-minimizing function.

Figure 14:
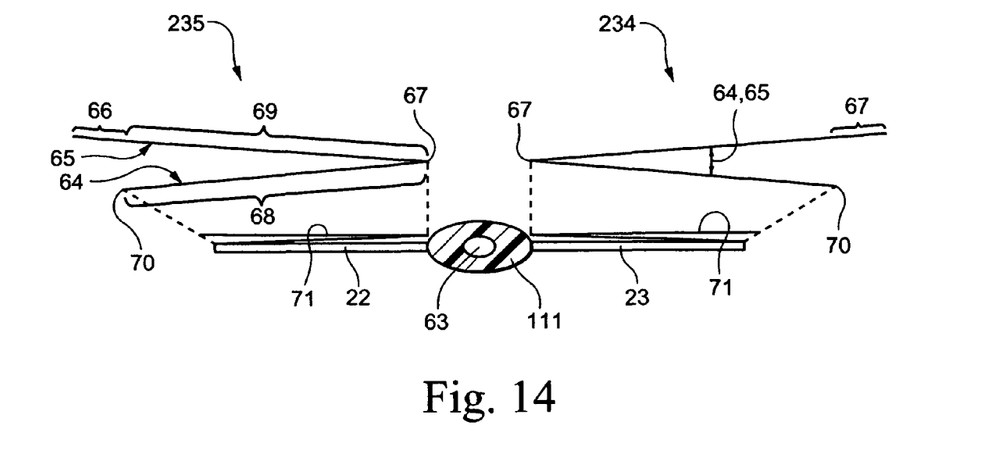
FIG. 14 is a posterior schematic view (with the receiving element in cross-section) of the stabilizing device of FIG. 3 showing a particular configuration of tape having cooperating adhesive and non-adhesive patterns so that the need for a release sheet is avoided.
Figure 15:
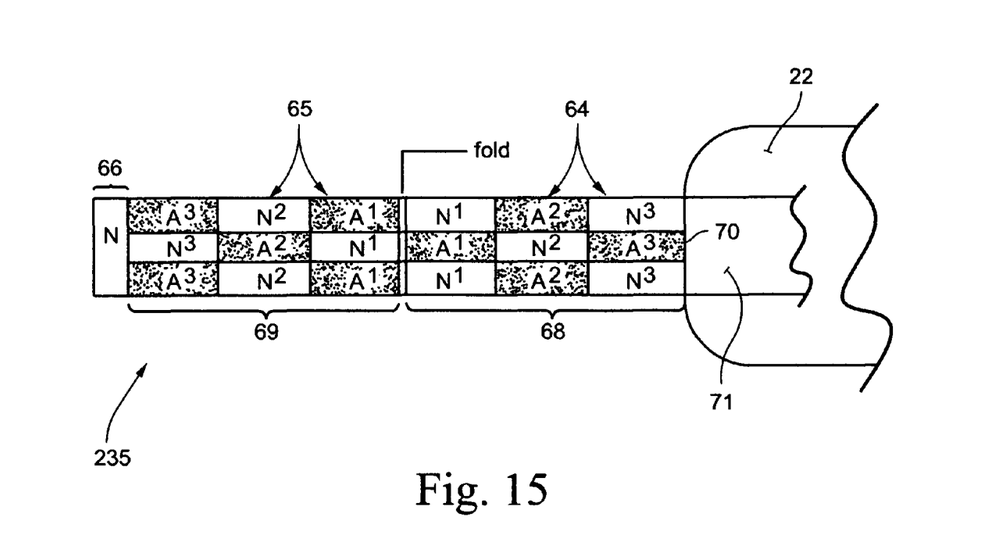
FIG. 15 is a bottom (inferior) view of one the pieces of tape of FIG. 14 showing the adhesive pattern in detail.

FIGS. 14 & 15 show an alternative configuration to the provision of release sheets 45, while still maintaining the adhesive associated with the tape strips sterile and inactive until use. FIGS. 14 & 15 illustrate this alternative with respect to modified lateral tape strips 234, 235, but it is to be understood that this modification is applicable to any one or more tape strips according to the invention. FIG. 14 shows the tubular interior 63 of the element 111, and wings 22, 23.

The tape strips 234, 235 each have bottom surfaces 64, 65 with a pattern of pressure sensitive adhesive A and release N sections (see FIG. 15), and have sections 68, 69 folded over at fold line 67 onto each other so that the adhesive A and release N sections operatively engage each other to maintain sterility and maintain the adhesive inactive until use. A lateral extension 66 is provided for each section 69 to facilitate unfolding of the sections 68, 69 when it is desired to secure the tape strips 64, 65 in place on skin S. After unfolding the sections 68, 69 are substantially coextensive with each other, as seen in FIG. 15, and extend away from the wings 22, 23. Then the adhesive sections A are pushed into contact with a patient's skin S and affix the tape strips 234, 235 thereto.

The strips 234, 235 may be affixed to the wings 22, 23 at a line 70 of each by any desired means. For example the strips 234, 235 may be integral with an extension 71 thereof which has its inferior surface positively adhesively secured to a wing 22, 23.

Figure 16:
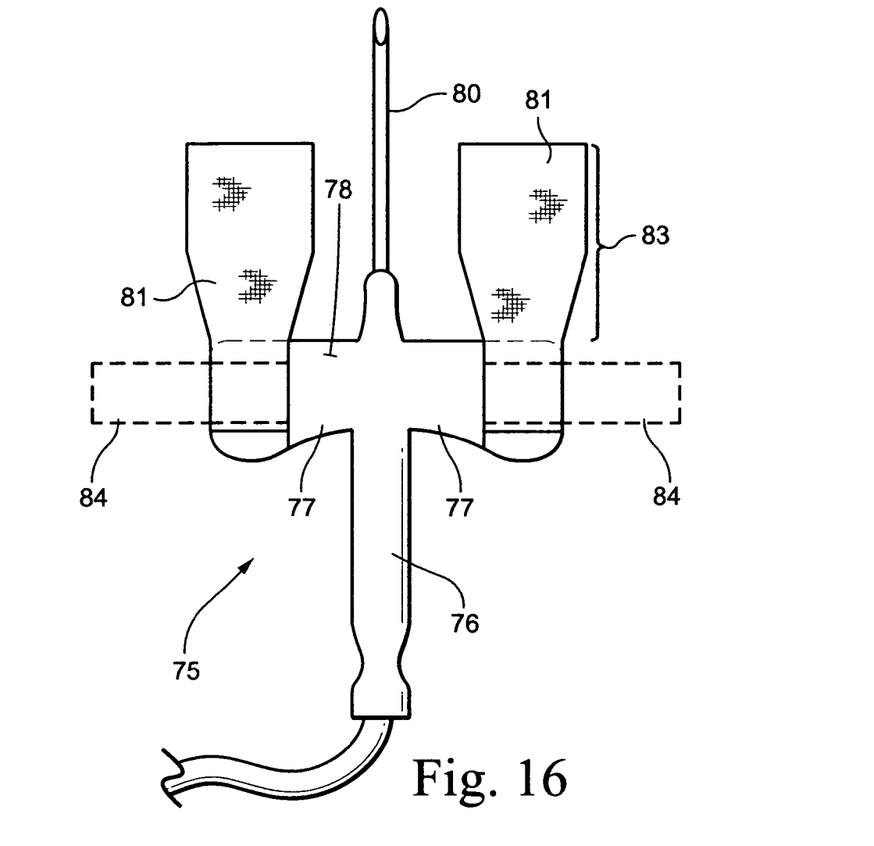
FIG. 16 is a top plan view of an exemplary butterfly catheter according to the invention with proximal strips of tape shown in solid line and optional additional lateral pieces shown in dotted line
Figure 17:
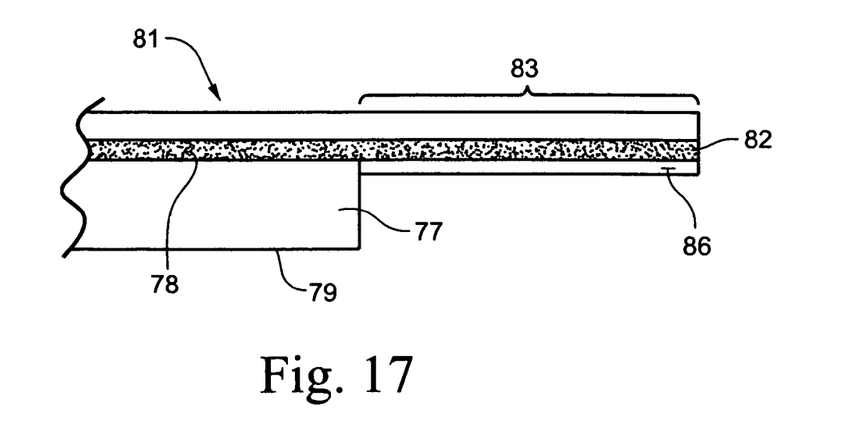
FIG. 17 is a side schematic view, with the components greatly enlarged for clarity of illustration, of a wing and proximal tape strip of the butterfly catheter of FIG. 16.
Figure 18:
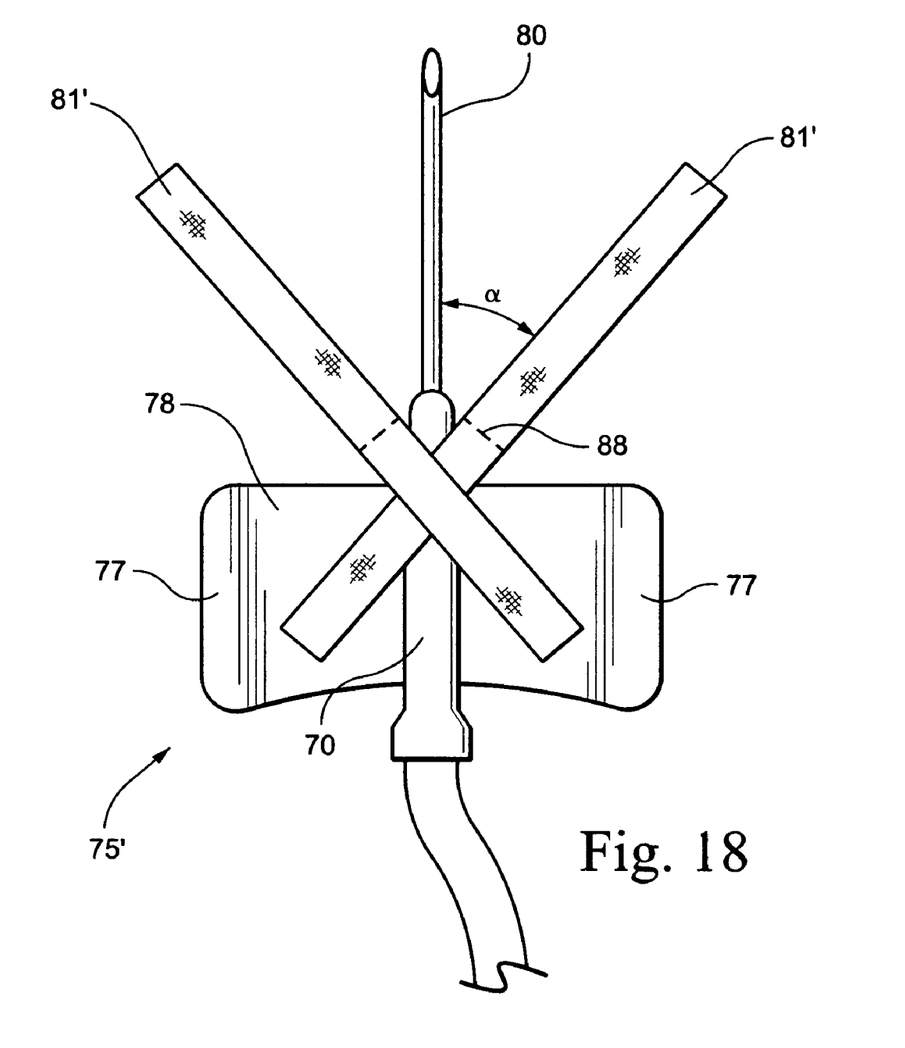
FIG. 18 is a view like that of FIG. 16 of a modified form of butterfly catheter according to the invention.

FIGS. 16-18 show another exemplary embodiment of a catheter or cannula stabilizing device according to the invention in the form of a butterfly catheter, shown generally at 75 or 75' in these figures.

The butterfly catheter 75 has a base 76 and highly flexible wings 77, each wing 77 with superior 78 (FIGS. 16 & 18) and inferior 79 (FIG. 17) surfaces. A hollow needle/catheter 80 extends from the base 76. These features are conventional for a butterfly catheter.

The catheter 75 according to the invention comprises at least two spaced, distinct, pieces of adhesive tape (81 in FIG. 16), with conventional sterile pressure sensitive adhesive 82 on inferior surfaces thereof. At least one piece of adhesive tape 81 is operatively connected to the superior surface 78 of each of the flexible wings 77, and each piece of tape 81 includes a portion 83 with sterile pressure sensitive adhesive overlapping a flexible wing 77 so that the adhesive 82 on the overlapping portion may be affixed to a patient's skin.

Preferably the at least two spaced, distinct, pieces of adhesive tape comprise proximal pieces, as shown for the pieces 81 in FIG. 16. The proximal pieces may have any desired shape, as shown for proximal pieces in the FIGS. 2, 3, & 8 embodiments. Also, preferably only two proximal pieces are provided. However if desired two lateral pieces—shown in dotted line at 84 in FIG. 16 and similar to the lateral pieces in the FIG. 3 embodiment—may be provided.

The adhesive 82 where it overlaps a wing 77 may be covered with a conventional release sheet 86, as illustrated in FIG. 17, which is a side view of a part of the catheter 75 with the thicknesses of the tape 81, adhesive 82, and release sheet 83 greatly exaggerated for clarity of illustration. The adhesive 82 and release sheet 83 may have the cooperating configurations such as described above with respect to the FIGS. 9, 12 & 13 embodiments. Alternatively, the tape 81 may have the fold-over configuration of FIGS. 14 & 15 so that no release sheet is necessary.

FIG. 18 shows an embodiment of a butterfly catheter 75' like that of FIG. 16 except that the proximal pieces of tape 81' extend at an angle α to the needle 80 of about 10-45 degrees. Fold lines 88 may be provided for the tape strips 81' comparable to the fold lines 50 in the FIGS. 8 & 9 embodiment.

The butterfly catheters 75, 75' are used just like conventional or prior art butterfly catheters (such as in U.S. Pat. No. 4,177,809 or 3,589,361) except that after insertion of the needle 80 the base 76 is stabilized in place quickly and effectively using the proximal stabilizing pieces of tape 81, 81'. This provides more secure, easier, and quicker affixation to the patient's skin than prior art butterfly catheters with adhesive components (such as in U.S. Pat. Nos. 3,589,361, 3,973, 565, 4,698,057 and 6,827,706). After removal of any blood flash or IV fluid from the patient's pre-sterilized skin, the lateral tape pieces 84 (if provided) may also be affixed to the patient's skin.

While the invention has been herein shown and described in what is presently conceived to be the most practical and preferred embodiment thereof, it is to be understood that many modifications are possible within the scope of the invention, including but not limited to changes in shape, material, configuration, and dimension. Therefore the claims are to be accorded the broadest interpretation possible consistent with the prior art to cover all equivalent methods and devices.

What is claimed is:

1. A stabilizing device for insertion, using a needle, and maintenance of a catheter or cannula, comprising:
    a first stabilizing element including a pair of bilateral wings and a catheter or cannula receiving element generally between said bilateral wings;
    a proximal stabilizing element operatively connected to at least one of said bilateral wings and including a sterile adhesive with a release covering overlapping said at least one of said bilateral wings for affixing said at least one of said bilateral wings to a patient to initially provide stability of the catheter or cannula during needle removal and then provide stability against displacement substantially for the duration that the catheter or cannula is inserted into a patient;
    a lateral stabilizing element distinct and spaced from said proximal stabilizing element, said lateral stabilizing element including a sterile adhesive with a release covering overlapping said at least one of said bilateral wings for affixing said at least one of said bilateral wings to a patient to provide primarily lateral and medial stability to the catheter or cannula in a patient; and
    wherein said proximal stabilizing element comprises at least first and second distinct and spaced tape strips with a pressure sensitive sterile adhesive with the release covering on portions thereof proximally overlapping said bilateral wings, one of said tape strips operatively connected to each of said bilateral wings.

2. A device as recited in claim 1 wherein said lateral stabilizing element comprises at least third and fourth distinct and spaced tape strips with a pressure sensitive sterile adhesive with the release covering on portions thereof laterally overlapping said bilateral wings, one of said at least third and fourth tape strips operatively connected to each of said bilateral wings.

3. A device as recited in claim 2 wherein said release coverings comprise separate release sheet coverings overlapping adhesive on each of said tape strips to maintain sterility; and further comprising an adhesive free portion at an edge of each of said tape strips to facilitate removal thereof after affixation to a patient's skin.

4. A device as recited in claim 2 wherein at least one of said tape strips has a bottom surface with a pattern of the pressure sensitive adhesive and release sections, and is folded over on itself so that said adhesive and release sections operatively engage each other to maintain sterility until unfolded to be affixed to a patient's skin.

5. A device as recited in claim 2 further comprising at least fifth and sixth distinct and spaced distal tape strips, one of said at least fifth and sixth tape strips operatively connected to each of said bilateral wings and having a portion thereof with a pressure sensitive sterile adhesive with a release covering distally overlapping a wing.

6. A device as recited in claim 2 wherein said proximal and lateral stabilizing elements consist essentially of said first through fourth tape strips.

7. A device as recited in claim 2 with said release coverings removed and in stabilizing contact with a patient's body, said pressure sensitive adhesives of said tape strips for adhesive contact with the patient's body to proximally and laterally stabilize said wings for contact with the patient's body.

8. A device as recited in claim 1 in combination with an angiocatheter or butterfly catheter received by said catheter or cannula receiving element.

9. A device as recited in claim 1 wherein said receiving element comprises a substantially tubular hub or base, and the catheter extending proximally from said hub or base; and in combination with a catheter insertion device having the needle extending through said hub or base and catheter.

10. A device as recited in claim 1 wherein said tape strips have non-adhesive portions thereof facilitating removal of said tape strips from a patient's skin when desired.

11. A device as recited in claim 1 wherein said first stabilizing element is non-adhesive.

12. A device as recited in claim 1 wherein said first stabilizing element is of medical grade plastic.

13. A device as recited in claim 1 wherein said first stabilizing element is of rigid material.

14. A device as recited in claim 13 wherein said first stabilizing element is non-adhesive.

15. A device as recited in claim 1 wherein said first stabilizing element is of semi-flexible material.

16. A device as recited in claim 15 wherein said first stabilizing element is non-adhesive.

17. A device as recited in claim 1 wherein said tape strips of said proximal stabilizing element are substantially parallel to the catheter or cannula received by said catheter or cannula receiving element.

18. A device as recited in claim 17 wherein said first stabilizing element is non-adhesive.

19. A device as recited in claim 1 wherein said receiving element comprises a substantially tubular hub or base, and the catheter extending proximally from said hub or base; and wherein said tape strips of said proximal stabilizing elements are substantially parallel to said catheter received by said hub or base.

* * * * *